(12) United States Patent
Silverstein et al.

(10) Patent No.: US 12,725,687 B2
(45) Date of Patent: Sep. 1, 2026

(54) UTILIZING WEARABLE DATA TO INFORM USER OF INSTRUCTIONAL CONTENT

(71) Applicant: INTERNATIONAL BUSINESS MACHINES CORPORATION, Armonk, NY (US)

(72) Inventors: Zachary A. Silverstein, Georgetown, TX (US); Logan Bailey, Atlanta, GA (US); Hemant Kumar Sivaswamy, Bangalore (IN); Brian P. Carey, Raleigh, NC (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 211 days.

(21) Appl. No.: 18/494,938

(22) Filed: Oct. 26, 2023

(65) Prior Publication Data

US 2025/0140359 A1 May 1, 2025

(51) Int. Cl.
*G16H 20/00* (2018.01)
*G16H 40/67* (2018.01)
*G16H 50/20* (2018.01)

(52) U.S. Cl.
CPC ............ *G16H 20/00* (2018.01); *G16H 40/67* (2018.01); *G16H 50/20* (2018.01)

(58) Field of Classification Search
CPC ........ G16H 40/67; G16H 50/30; G16H 50/70; G16H 80/00; G16H 20/00; G16H 50/50
See application file for complete search history.

(56) References Cited

U.S. PATENT DOCUMENTS 9,030,495 B2 5/2015 Mcculloch
10,720,159 B1 7/2020 Sindhwani
(Continued)

FOREIGN PATENT DOCUMENTS

CN 110138959 B 2/2022
KR 102415605 B1 6/2022

OTHER PUBLICATIONS

Torrado JC, Gomez J, Montoro G. Emotional Self-Regulation of Individuals with Autism Spectrum Disorders: Smartwatches for Monitoring and Interaction. Sensors (Basel). Jun. 11, 2017;17(6):1359. doi: 10.3390/s17061359. PMID: 28604607; PMCID: PMC5492838 (Year: 2017).*

(Continued)

*Primary Examiner* — Joseph D Burgess
(74) *Attorney, Agent, or Firm* — Steven M. Bouknight

(57) ABSTRACT

A method for automatically providing instructional content based on wearable data from a wearable device is provided. The method may include automatically tracking and receiving, via the wearable device, real-time wearable data associated with a user and a detected user activity including automatically detecting body sensor data associated with the user and corresponding to the detected user activity. The method may also include automatically determining whether the tracked and received real-time wearable data associated with the user and the user activity indicates a user frustration event. The method may further include in response to automatically determining that the tracked and received real-time wearable data associated with the user and the user activity indicates the user frustration event, automatically retrieving and presenting the instructional content from instructional material related to the user activity and the user frustration event.

17 Claims, 2 Drawing Sheets

(56) References Cited

U.S. PATENT DOCUMENTS

| | | | | |
|---|---|---|---|---|
| 2017/0228596 | A1 | 8/2017 | Wexler | |
| 2018/0101776 | A1* | 4/2018 | Osotio | G06F 16/258 |
| 2020/0126141 | A1* | 4/2020 | Bostick | G06Q 30/0627 |
| 2020/0160399 | A1* | 5/2020 | Rakshit | G10L 15/26 |
| 2020/0390337 | A1* | 12/2020 | Frank | A61B 5/0205 |
| 2021/0251554 | A1* | 8/2021 | Tal | G16H 50/20 |
| 2022/0383864 | A1 | 12/2022 | Gruber | |

OTHER PUBLICATIONS

Bloomberg Business, "Wearable Technology Market to Hit $186.14 Billion by 2030: Grand View Research, Inc.", Nov. 28, 2022, https://www.bloomberg.com/press-releases/2022-11-28/wearable-technology-market-to-hit-186-14-billion-by-2030-grand-view-research-inc.

Disclosed Anonymously, "AI Assistance Interaction with Visual Simulation on an Edge Device", An IP.com Prior Art Database Technical Disclosure, IP.com No. IPCOM000262813D, Publication Date: Jul. 1, 2020, 6 pages.

Disclosed Anonymously, "Identification of Smart Devices in Proximity to a User", An IP.com Prior Art Database Technical Disclosure, IP.com No. IPCOM000252057D, Publication Date: Dec. 14, 2017, 9 pages.

Disclosed Anonymously, "Method and System for AI Voice Assistance System to Offer Help," An IP.com Prior Art Database Technical Disclosure, IP.com No. IPCOM000265423D, Publication Date: Apr. 8, 2021, 5 pages.

Globe Newswire, "Wearable Technology Market Size to Reach USD 392.4 Bn by 2030", Aug. 15, 2022, https://www.globenewswire.com/news-release/2022/08/15/2497937/0/en/Wearable-Technology-Market-Size-to-Reach-USD-392-4-Bn-by-2030.html.

IBM, "IBM Watson IoT Platform ", accessed Jul. 21, 2023, 4 pages, https://internetofthings.ibmcloud.com/.

Kato et al., "Secure and Efficient Trajectory-Based Contact Tracing using Trusted Hardware", arXiv:2010.13381v2, Nov. 4, 2020, 10 pages.

RDRR.Io, "Geohash", Tools for Geohash Creation and Manipulation, Accessed on Jul. 21, 2023, 2 pages, https://rdrr.io/cran/geohash/.

Serafino et al., "Digital contact tracing and network theory to stop the spread of COVID-19 using big-data on human mobility geolocalization", PLOS Computational Biology, Research Article, Apr. 11, 2022, 13 pages.

* cited by examiner

UTILIZING WEARABLE DATA TO INFORM USER OF INSTRUCTIONAL CONTENT

BACKGROUND

The present invention relates generally to the field of computing, and more specifically, to dynamically providing relevant instructional content to a user on a computing device in response to performing, via a wearable device, real-time detection and prediction of a user difficulty during an activity.

Generally, wearable technology is any kind of computer or electronic device designed to be worn on the user's body. Such devices can take many different forms, including jewelry, accessories, medical devices, and clothing or elements of clothing. The term wearable computing implies processing or communications capabilities, but the sophistication among wearables can vary. For example, modern wearable technology falls under a broad spectrum of usability, including smartwatches, fitness trackers such as the Fitbit Charge, virtual reality (VR) headsets, smart jewelry, web-enabled glasses and Bluetooth headsets. Wearables work differently, based on the category they belong to, such as health, fitness or entertainment.

Predominantly, wearable technology functions by incorporating microprocessors, batteries and connectivity to the internet so the collected data can be synced with other electronics, such as mobile devices or laptops. Wearables are further embedded with built-in sensors that keep track of body sensor data such as bodily movements, provide biometric identification or assist with location tracking. For example, activity trackers or smartwatches—the most common types of wearables—come with a strap that wraps around the user's wrist to monitor their physical activities or vitals throughout the day.

While most wearables are either worn on the body or are attached to clothing, some function without any physical contact with the user. Cell phones, smart tags or computers can still be carried around and track user movements. Other wearables use remote smart sensors and accelerometers to track movements and speed, and some use optical sensors for measuring heart rate or glucose levels. A common factor among these technology wearables is the fact they all monitor data in real time. Furthermore, while consumer electronics such as smartwatches and fitness trackers are prominent use cases for wearable technology, recent advancements in internet of things (IoT) devices and AI have allowed wearable technology to be incorporated into all types of scenarios—from healthcare, navigation systems, consumer goods and professional sports.

SUMMARY

A method for automatically providing instructional content based on wearable data from a wearable device is provided. The method may further include automatically tracking and receiving, via the wearable device, real-time wearable data associated with a user and a detected user activity, wherein automatically tracking and receiving the real-time wearable data associated with the user and the detected user activity further comprises automatically detecting body sensor data associated with the user and corresponding to the detected user activity. The method may also include automatically determining whether the tracked and received real-time wearable data associated with the user and the user activity indicates a user frustration event. The method may further include in response to automatically determining that the tracked and received real-time wearable data associated with the user and the user activity indicates the user frustration event, automatically retrieving and presenting the instructional content from instructional material related to the user activity and the user frustration event.

A computer system for automatically providing instructional content based on wearable data from a wearable device is provided. The computer system may include one or more processors, one or more computer-readable memories, one or more computer-readable tangible storage devices, and program instructions stored on at least one of the one or more storage devices for execution by at least one of the one or more processors via at least one of the one or more memories, whereby the computer system is capable of performing a method. The method may further include automatically tracking and receiving, via the wearable device, real-time wearable data associated with a user and a detected user activity, wherein automatically tracking and receiving the real-time wearable data associated with the user and the detected user activity further comprises automatically detecting body sensor data associated with the user and corresponding to the detected user activity. The method may also include automatically determining whether the tracked and received real-time wearable data associated with the user and the user activity indicates a user frustration event. The method may further include in response to automatically determining that the tracked and received real-time wearable data associated with the user and the user activity indicates the user frustration event, automatically retrieving and presenting the instructional content from instructional material related to the user activity and the user frustration event.

A computer program product for automatically providing instructional content based on wearable data from a wearable device is provided. The computer program product may include one or more computer-readable storage devices and program instructions stored on at least one of the one or more tangible storage devices, the program instructions executable by a processor. The computer program product may further include program instructions to automatically track and receive, via the wearable device, real-time wearable data associated with a user and a detected user activity, wherein automatically tracking and receiving the real-time wearable data associated with the user and the detected user activity further comprises automatically detecting body sensor data associated with the user and corresponding to the detected user activity. The computer program product may also include program instructions to automatically determine whether the tracked and received real-time wearable data associated with the user and the user activity indicates a user frustration event. The computer program product may further include program instructions to, in response to automatically determining that the tracked and received real-time wearable data associated with the user and the user activity indicates the user frustration event, automatically retrieve and present the instructional content from instructional material related to the user activity and the user frustration event.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings.

DETAILED DESCRIPTION

Figure 1:
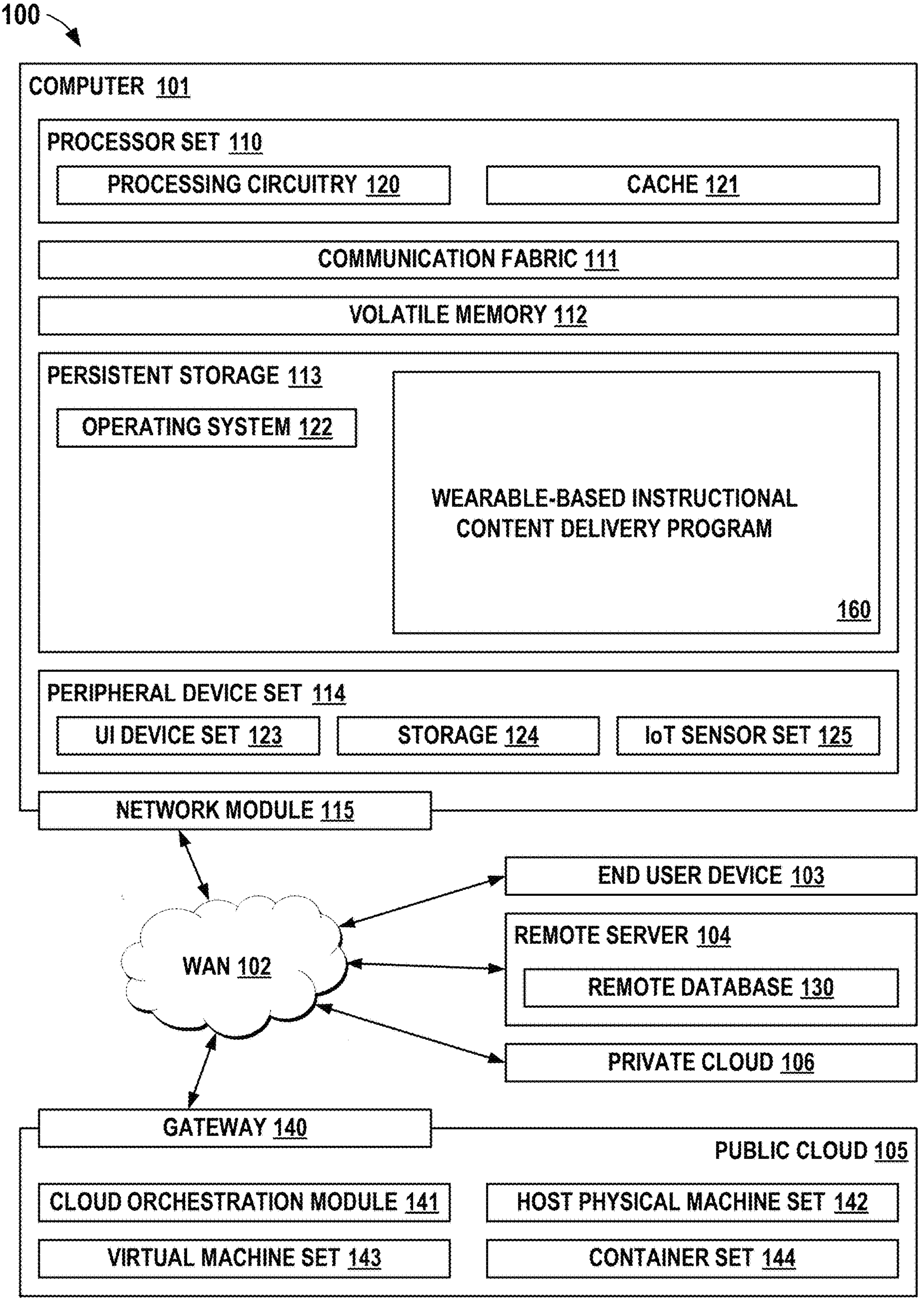
FIG. 1 illustrates an exemplary computing environment according to one embodiment.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. In the description, details of well-known features and techniques may be omitted to avoid unnecessarily obscuring the presented embodiments.

Embodiments of the present invention relate generally to the field of computing, and more particularly, to automatically prompting and providing a user relevant instructional content on a computing device in response to detecting and predicting, in real-time via a wearable device, user difficulty during an activity. Specifically, the present invention may improve the technical field associated with wearable technology and functions by correlating data associated with wearable devices and other computer devices with real-time tracking and detection of user frustration and/or difficulty based on body sensor data and other data with regard to an activity and then provide a user with instructional content at an optimal time in response detecting such difficulty. Specifically, for example, the present invention may include, leverage, and/or interface with online instructional material such as user manuals, guided tutorials, new feature walk-throughs, help menus, onscreen chat, user surveys, report a problem within a feature, etc. Furthermore, and as previously described, the present invention may be incorporated with wearable and other computer devices having built-in sensors and other electrical components that keep track of body sensor data such as bodily position and movements, provide biometric identification, as well as identify speech through speech recognition, and/or assist in location tracking for tracking and receiving real-time user data including a user's movement, bodily position, location, speech and other data. Then, the present invention may correlate and associate real-time data points from the tracked and received real-time user data with historical data associated with the user, as well as correlate and associate the real-time data points with other tracked data associated with other users, products, and services, to predict and identify times of user difficulty, frustration, and/or confusion with a product and/or service. Thereafter, based on detection of a real-time data point that is correlated and associated with historical data and/or other tracked data that has been identified as a time of user difficulty/frustration/confusion, the present invention may prompt and provide the user with the instructional content based on the online instructional material.

As previously described, while consumer electronics such as smartwatches and fitness trackers are prominent use cases for wearable technology, recent advancements in internet of things (IoT) devices and AI have allowed wearable technology to be incorporated into all types of different use cases including healthcare, navigation systems, consumer goods, and professional sports. In addition, the software industry has a wide range of product analytics tools and apps to help companies ensure proper use and satisfaction of products in the different use cases. For example, among these tools may include instructional documentation and user feedback within the software. However, the wearable device industry has not benefitted from such tools since wearables, including some IoT devices, are often small and do not always have the level of input and feedback gathering that is possible with traditional software that is run on a computer or smart device with digital input/output screens.

On the contrary, wearable devices can provide a tremendous amount of context about a user and/or an activity, such as when a user is interacting with a newly purchased item that is smart, physical, or otherwise. However, sometimes users may not understand how an item/product works or is assembled and may, in turn, fumble around with the product or try certain actions without much success. This can be very frustrating for a user and can lead the user to print manual instructions or search for online instructional material to assist the user with the item. As such, it may be advantageous to use data from wearable devices to detect discrepancies and/or difficulty with a user activity and, in turn, know when to provide instructional content to the user for guidance.

More specifically, it may be advantageous, among other things, to provide a method, computer system, and computer program product for automatically tracking and receiving, via the wearable device, real-time wearable data associated with a user and a detected user activity, wherein automatically tracking and receiving the real-time wearable data associated with the user and the detected user activity further comprises automatically detecting body sensor data associated with the user and corresponding to the detected user activity. The method, computer system, and computer program product may automatically determine whether the tracked and received real-time wearable data associated with the user and the user activity indicates a user frustration event. The method, computer system, and computer program product may, in response to automatically determining that the tracked and received real-time wearable data associated with the user and the user activity indicates the user frustration event, automatically retrieve and present the instructional content from instructional material related to the user activity and the user frustration event.

The present invention may be a system, a method, and/or a computer program product at any possible technical detail level of integration. The computer program product may include a computer readable storage medium (or media) having computer readable program instructions thereon for causing a processor to carry out aspects of the present invention.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed concurrently or substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The following described exemplary embodiments provide a system, method, and program product to determine whether directional input is received along with a query and, accordingly, adjust presented display content to include a referenced object in a center of a screen of a primary device.

Referring to FIG. 1, an exemplary computing environment 100 is depicted, according to at least one embodiment. Computing environment 100 contains an example of an environment for the execution of at least some of the computer code involved in performing the inventive methods, such as an wearable-based instructional content delivery program 160. In addition to block 160, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and block 160, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

Computer 101 may take the form of a desktop computer, laptop computer, tablet computer, smart phone, smart watch or other wearable computer (such as a wearable headset), mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

Processor set 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located “off chip.”

In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in block 160 in persistent storage 113.

Communication fabric 111 is the signal conduction paths that allow the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

Volatile memory 112 is any type of volatile memory now known or to be developed in the future. Examples include dynamic type random access memory (RAM) or static type RAM. Typically, the volatile memory 112 is characterized by random access, but this is not required unless affirmatively indicated. In computer 101, the volatile memory 112 is located in a single package and is internal to computer 101, but, alternatively or additionally, the volatile memory 112 may be distributed over multiple packages and/or located externally with respect to computer 101.

Persistent storage 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage 113 allows writing of data, deletion of data and re-writing of data. Some familiar forms of persistent storage 113 include magnetic disks and solid state storage devices. Operating system 122 may take several forms, such as various known proprietary operating systems or open source Portable Operating System Interface type operating systems that employ a kernel. The code included in block 160 typically includes at least some of the computer code involved in performing the inventive methods.

Peripheral device set 114 includes the set of peripheral devices of computer 101. Data communication connections between the peripheral devices 114 and the other components of computer 101 may be implemented in various ways, such as Bluetooth connections, Near-Field Communication (NFC) connections, connections made by cables (such as universal serial bus (USB) type cables), insertion type connections (for example, secure digital (SD) card), connections made through local area communication networks and even connections made through wide area networks such as the internet. In various embodiments, UI device set 123 may include components such as a display screen, speaker, microphone, wearable devices (such as goggles, headsets, and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database), this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector and/or accelerometer.

Network module 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN may be replaced and/or supplemented by local area networks (LANs) designed to communicate data between devices located in a local area, such as a Wi-Fi network. The WAN 102 and/or LANs typically include computer hardware such as copper transmission cables, optical transmission fibers, wireless transmission, routers, firewalls, switches, gateway computers and edge servers.

End user device (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

Remote server 104 is any computer system that serves at least some data and/or functionality to computer 101.

Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

Public cloud 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

Private cloud 106 is similar to public cloud 105, except that the computing resources are only available for use by a single enterprise. While private cloud 106 is depicted as being in communication with WAN 102, in other embodiments the private cloud 106 may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

According to the present embodiment, the wearable-based instructional content delivery program 160 may be a program/code capable of providing a method, computer system, and computer program product for automatically tracking and receiving, via the wearable device, real-time wearable data associated with a user and a detected user activity, wherein automatically tracking and receiving the real-time wearable data associated with the user and the detected user activity further comprises automatically detecting body sensor data associated with the user and corresponding to the detected user activity. The wearable-based instructional content delivery program 160 may further automatically determine whether the tracked and received real-time wearable data associated with the user and the user activity indicates a user frustration event. The wearable-based instructional content delivery program 160 may also, in response to automatically determining that the tracked and received real-time wearable data associated with the user and the user activity indicates the user frustration event, automatically retrieve and present the instructional content from instructional material related to the user activity and the user frustration event.

Furthermore, notwithstanding depiction in computer 101, the wearable-based instructional content delivery program 160 may be stored in and/or executed by, individually or in any combination, with end user device 103, remote server 104, public cloud 105, and private cloud 106. The wearable-based instructional content delivery program is explained in further detail below with respect to FIG. 2.

Figure 2:
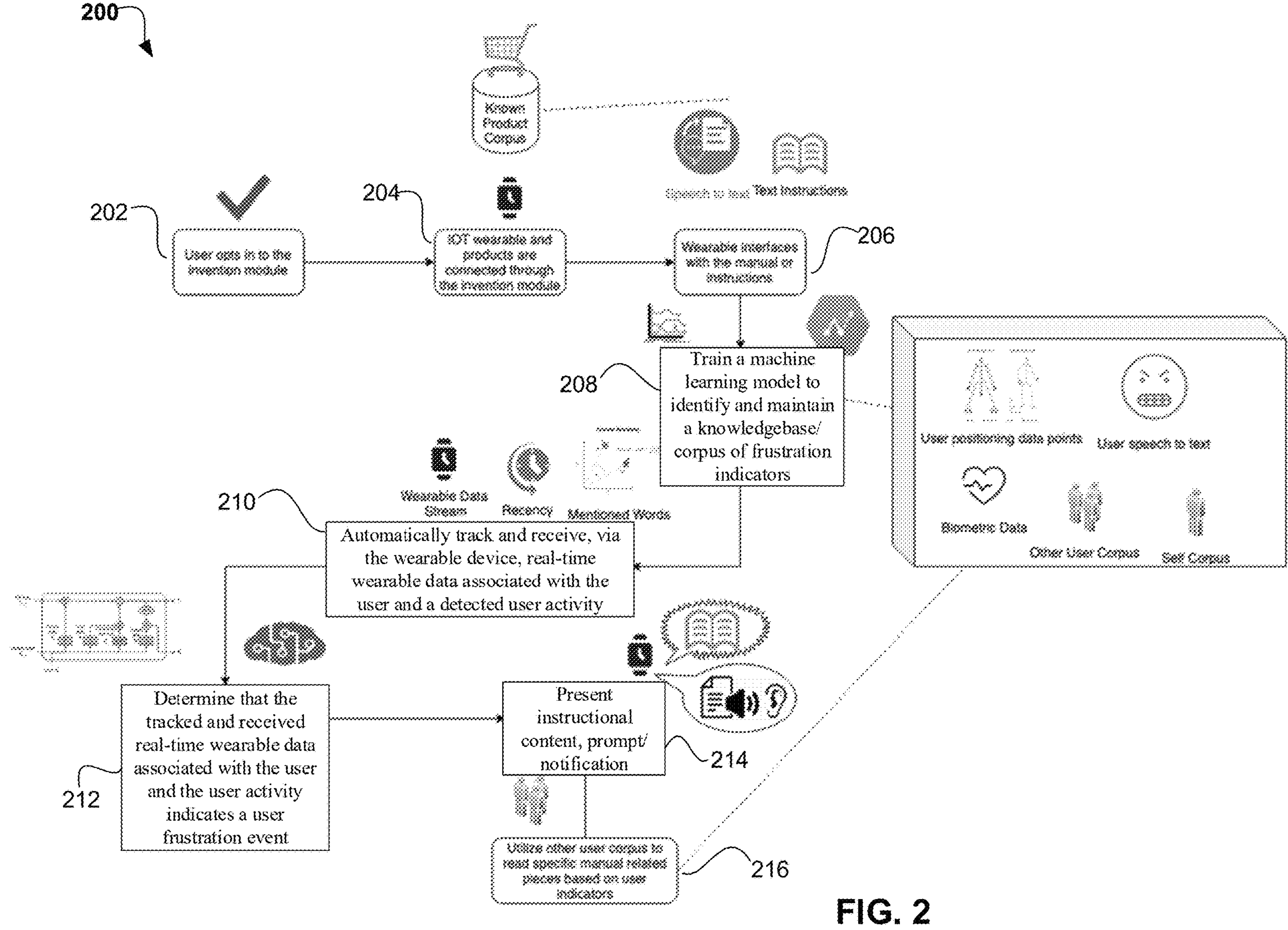
FIG. 2 is an operational flowchart indicating the steps carried out by a program for automatically providing instructional content based on wearable data from a wearable device according to one embodiment.

Referring now to FIG. 2, an operational flowchart 200 illustrating operations carried out by a program for automatically providing instructional content based on wearable data from a wearable device is depicted. According to one embodiment, the wearable-based instructional content delivery program 160 may run on a computer (such as computer 101 described in FIG. 1) which may include a wearable device such as a smartwatch. Furthermore, as depicted at 202, the wearable-based instructional content delivery program 160 may prompt a user to opt into the wearable-based instructional content delivery program 160, whereby opting in may prompt the wearable-based instructional content delivery program 160 to generate a user profile associated with the user to track and receive user data. According to one embodiment, the wearable-based instructional content delivery program 160 may generate multiple user profiles for each user opting into the wearable-based instructional content delivery program 160 and may use certain data collected from each user profile to assist in providing instructional content to a specific user.

As depicted at 204, the wearable-based instructional content delivery program 160 may connect and correlate the wearable device (such as the smartwatch) with other computer devices associated with the user (mobile phone, laptop computer, etc.), to, for example, track and receive user data associated with a user and a user activity. For example, the wearable-based instructional content delivery program 160 may track and receive user data including wearable data that may further include body sensor data such as user body position data, movement data, and biometric data, as well as user speech data and user location data. The wearable-based instructional content delivery program 160 may also track and receive other user data which may be associated with the user's computer devices including user purchase history, email and messaging data, and internet search history. The wearable-based instructional content delivery program 160 may establish connections and correlate data between the wearable and other computer devices including the body sensor data and other data which may, in turn, be interpreted and contextualized (using machine learning) by the wearable-based instructional content delivery program 160. Furthermore, the wearable-based instructional content delivery program 160 may use the tracked and received user data from the wearable and other computer devices to identify products/items associated with a user by, for example, tracking the user purchase history, internet search history, email and messaging data (such as purchase confirmation emails/messages and/or package tracking emails/messages), and user speech that may identify other products and/other items. Similarly, with respect to user speech, the wearable-based instructional content delivery program 160 may further include speech analysis tools such as sentiment analysis and other natural language processing tools for further analyzing received speech and text to, for example, contextualize speech and determine an emotional tone of the speech or text (such as an emotional tone of positive, negative, neutral, frustration, anger, confusion, etc.).

Additionally, and as previously described, the wearable-based instructional content delivery program 160 may further use the wearable devices and wearable data to detect whether a user is interacting with a product/item and/or performing an activity based on the tracked and received user data. For example, according to one embodiment, the wearable-based instructional content delivery program 160 may detect that a user purchased a new product such as headphones, furniture, and/or other physical products, for example, by identifying an email confirmation of a purchase of the new product, a delivery status of the new product, and/or the user location data associated with the user (such as detecting a user traveling to and from a certain store). According to one embodiment, by tracking wearable data including body sensor data such as user body position and user movement data via the wearable device, the wearable-based instructional content delivery program 160 may also detect when a user may be interacting with a product/item and/or performing an activity such as assembling the new product and/or generally trying the new product. Thus, for example, based on the connections between the wearable and other computer devices associated with the user, the wearable-based instructional content delivery program 160 may aggregate various user data from the tracked and received user data (including the wearable data) to determine which products/items are associated with the user and when the user may be interacting with a specific product/item.

As depicted at 206, the wearable-based instructional content delivery program 160 may further identify, include, and retrieve instructional material which may be associated with a product/item and enable the wearable device to interface with the instructional material. Generally, for example, a product such as headphones may have instructional material such as a manual for using and connecting the headphones. Similarly, furniture may have instructional material for assembling the furniture, and even an exercise may have instructional material on properly performing the exercise. As previously described, the wearable-based instructional content delivery program 160 may track and identify devices and other products/items that may be associated with a user through, for example, tracking user purchase history, internet search history, email and messaging data, and user speech that may identify different products and/other items. Accordingly, based on identifying products/items associated with the user, the wearable-based instructional content delivery program 160 may correspondingly identify instructional material such as manuals and other content (including media content such as pictures, audio and video) that may be associated with a product/item. For example, in response to identifying a product/item associated with a user, the wearable-based instructional content delivery program 160 may correspondingly identify and retrieve instructional material associated with the product/item from, according to one embodiment, online sources including websites, online databases and files. According to one embodiment, the wearable-based instructional content delivery program 160 may store the retrieved instructional material on a database and/or cloud-based server associated with the wearable-based instructional content delivery program 160 (which may include the various databases, storage, and servers described in FIG. 1). Also, according to one embodiment, the wearable-based instructional content delivery program 160 may allow the instructional material associated with a product/item to be uploaded to the database and/or cloud-based server associated with the wearable-based instructional content delivery program 160 by, for example, presenting a user interface that allows uploading of a document and/or media content which may be subsequently stored. In turn, the wearable-based instructional content delivery program 160 may use the retrieved and/or stored instructional material to generate a knowledgebase/corpus of instructional material for determining expected interaction with a device/product/item.

As such, and based in part on the instructional material and knowledgebase/corpus of expected interaction, the wearable-based instructional content delivery program 160 may train a machine learning model, such as a long short-term memory (LSTM) model, to identify and classify wearable data that indicates user frustration with a product/item, as well as identify deviations from instructional material, which may further include identifying behavioral triggers indicative of the user frustration. Specifically, and as depicted at 208, the wearable-based instructional content delivery program 160 may include and train the machine learning model to identify and maintain a knowledgebase/corpus of frustration indicators that identifies behavioral patterns and/or triggers detected from the wearable data which may indicate user frustration with a device/product/item. As previously described, the wearable-based instructional content delivery program 160 may track and receive wearable data including body sensor data such as user body movements, user biometric data, user speech data, and user location data. The wearable-based instructional content delivery program 160 may also track and receive other data including user purchase history, email and messaging data, and internet search history. In turn, the wearable-based instructional content delivery program 160 may use the various tracked and received user data to determine whether a user is interacting with a device/product/item.

For example, and as previously described, the wearable-based instructional content delivery program 160 may determine from email/messaging data that a user recently purchased headphones based on a purchase confirmation email/message. Also, for example, the wearable-based instructional content delivery program 160 may determine, via the wearable device, that a user is continuously raising their arms/hands towards their ears in a certain time interval within an hour of the purchasing confirmation email as well as may determine from speech a user stating, "why won't these headphones connect to this other device." The wearable-based instructional content delivery program 160 may, therefore, determine that the user is interacting with the recently purchased headphones. The wearable-based instructional content delivery program 160 may also determine that a user may be frustrated. For example, in addition to detecting the aforementioned speech ("why won't these headphones connect to this other device"), the wearable-based instructional content delivery program 160 may further detect, via the wearable device and using speech analysis tools, the emotional tone of the speech which may further indicate the user being annoyed and/or frustrated as well as indicate a need for assistance. Furthermore, the wearable-based instructional content delivery program 160 may also detect body sensor data including biometric data, via the wearable device, such as detecting an increased heart rate and/or increase in blood pressure to a certain threshold level which may further provide an indication of frustration and/or confusion from the user.

As such, based on the detected wearable data indicating user frustration and/or a need for assistance, the wearable-based instructional content delivery program 160 may identify and retrieve instructional material, for example, from the online sources and/or from stored instructional material in the generated knowledgebase/corpus of instructional material. For example, the wearable-based instructional content delivery program 160 may identify a specific type of headphone that the user is interacting with based on the tracked and received user data such as the email/messaging data that includes the purchase confirmation. Accordingly, the wearable-based instructional content delivery program 160 may identify and retrieve instructional material associated with the specific type of headphone. The wearable-based instructional content delivery program 160 may also determine a specific step and/or activity that is causing the user frustration based on the tracked user data. For example, using the NLP and machine learning algorithms on the speech—"why won't these headphones connect to this other device"—the wearable-based instructional content delivery program 160 may interpret such speech and determine that the user is attempting to connect the purchased headphones to a device and/or simultaneously to a second device. In turn, the wearable-based instructional content delivery program 160 may identify specific instructional content from the instructional material related to the purchased headphones and prompt the user on the wearable device. For example, the prompt (i.e. notification) may include a presented question on a display of the wearable device such as, "Would you like help with your current activity" or "Would you like help with your current item," as well as include selectable user interface icons that include "Yes" and "No." According to one embodiment, in response to selecting "Yes," the wearable-based instructional content delivery program 160 may proceed with providing the instructional content. According to one embodiment, and as previously described, the wearable-based instructional content delivery program 160 may specifically provide instructions related to the specific step and/or activity that is causing the user frustration based on, for example, the speech indicating a user trying to connect to a device. According to one embodiment, and in certain instances of uncertainty on which instructional content to provide (which may be based on a threshold percentage, such as the machine learning model having less than a 86% certainty), the wearable-based instructional content delivery program 160 may further prompt the user on the wearable device by asking the user to "provide additional information," which may then include capturing user speech. For example, in response to further prompting the user to provide the additional information, the wearable-based instructional content delivery program 160 may capture speech from the user such as, "I am trying to simultaneously connect my headphones to a second device."

The wearable-based instructional content delivery program 160 may further identify specific steps causing user frustration based on the body sensor data that includes the user body position and/or body movement captured during a certain time interval of detected user frustration. In another example, in the case of similarly identifying that a user recently purchased furniture, the wearable-based instructional content delivery program 160 may similarly identify that the user is assembling the furniture based on body sensor data such as user bodily position and movement that may coincide with instructional material and expected interaction associated with the furniture from the knowledgebase/corpus of instructional material. The wearable-based instructional content delivery program 160 may also similarly detect at a certain time interval of user frustration from elevated biometric data and/or speech including specific language and a certain emotional tone indicative of frustration. As such, the wearable-based instructional content delivery program 160 may identify the user bodily position and movement with regard to the product/item (and/or user activity) during the detected frustration to determine a specific step that may be associated with such detected position and/or movement.

In turn, and as previously described, the wearable-based instructional content delivery program 160 may specifically provide instructions related to the specific step and/or activity determined to cause the user frustration based on the wearable data. According to one embodiment, the wearable-based instructional content delivery program 160 may specifically provide the instructional content to the user by presenting the instructional content via audio on the wearable device. According to one embodiment, the wearable-based instructional content delivery program 160 may specifically provide the instructional content on one or more other computer devices associated with the user such as displaying the instructional content on a mobile phone. Also, according to one embodiment, the wearable-based instructional content delivery program 160 may allow a user to select which device to present and/or display the instructional content such as by including a user interface for selecting user preferences and setting a default device and/or by further prompting the user to select a device in response to selecting "Yes" to receiving the instructional content. The wearable-based instructional content delivery program 160 may further prompt the user to provide feedback to, for example, determine whether the instructional content helped the user. Also, according to one embodiment, the wearable-based instructional content delivery program 160 may detect user feedback by determining whether the user was satisfied with the instructional content based on tracked and received user data such as detecting that the user is following instructions based on detected bodily position and/or movement and/or detecting speech such as "this helps" or "it works."

Accordingly, and as previously described at 208, the wearable-based instructional content delivery program 160 may include and train the machine learning model to identify and maintain a knowledgebase/corpus of frustration indicators that identifies behavioral patterns and/or triggers detected from the wearable data indicating user frustration with a device/product/item (and/or a step or certain interaction with the device/product/item). Specifically, according to one embodiment, the behavioral patterns/triggers may include the detected user data, including the detected wearable data, that prompted the wearable-based instructional content delivery program 160 to identify a user as being frustration and a user activity (and/or specific step) as causing the user frustration. More specifically, the wearable-based instructional content delivery program 160 may capture, correlate, and associate information associated with the user data, the wearable data from the wearable device that was determined as indicating user frustration, the detected type of product/item that the user was interacting with, the instructional material associated with the product/item, the provided instructional content used to resolve the detected user frustration, timestamp data, and any received user feedback. For example, the wearable-based instructional content delivery program 160 may use the machine learning model, which again may include a LSTM model, to determine the user data and the sequential steps that a user performed from the wearable data (which may be based on certain time interval leading up, during, and following the frustration event), determine a certain time point or step that the user started experiencing frustration (based, for example, on the detected hand movement and/or speech), and may identify such step as a difficult step that other users may experience going forward. Thus, the wearable-based instructional content delivery program 160 may accordingly log the correlated and associated information as events in the corpus of frustration indicators and similarly log correlated and associated events involving other users and interactions with other products and performed activities. As such, according to one embodiment, the frustration indicators may include data points from events that may be classified as involving user frustration with a product/item, and more specifically, with user interaction and/or user activity involving the product/item whereby assistance was automatically provided. As previously described at 202, the wearable-based instructional content delivery program 160 may generate multiple user profiles for each user opting into the wearable-based instructional content delivery program 160 and may use certain data collected from each user profile to assist in providing instructional content to a specific user. Therefore, the more data collected, the more the wearable-based instructional content delivery program 160 may use to assist in providing instructional content to a user. In turn, the wearable-based instructional content delivery program 160 may use the machine learning model to apply the correlated and associated information and the events representative of frustration indicators to tracked and received real-time data for predicting and resolving similar events.

Specifically, and as depicted at 210, the wearable-based instructional content delivery program 160 may automatically track and receive, via the wearable device, real-time wearable data associated with the user and a detected user activity, wherein automatically tracking and receiving the real-time wearable data associated with the user and the user activity further comprises automatically detecting body sensor data associated with the user and corresponding to the user activity. According to one embodiment, the user activity may include user actions (such as an exercise) and/or user interaction with a device, product, and/or other item. Thus, similar to the previous example, the wearable-based instructional content delivery program 160 may determine, in real-time via the wearable device, body sensor data that may include a user continuously placing their arms/hands towards their cars, elevated biometric data (such as elevated heart rate and/or blood pressure to certain threshold level), and user speech such as, "ugh, these headphones won't connect to my computer as well." Similarly, the wearable-based instructional content delivery program 160 may have determined from email/messaging data that a user recently purchased headphones based on a confirmation email/message.

As such, at 212, the wearable-based instructional content delivery program 160 may automatically determine whether the tracked and received real-time wearable data associated with the user and the user activity indicates a user frustration event. Specifically, the determining may further include comparing the tracked and received real-time wearable data to previously tracked and received wearable data (including previously stored user frustration event data) that is associated with the user and other users from the knowledgebase/corpus of frustration indicators. As previously described, the knowledgebase/corpus of frustration indicators may include captured and correlated information associated with a user event including information associated with user data, wearable data from a wearable device associated with the user that was determined as indicating user frustration, a detected type of product/item that the user was interacting with, instructional material associated with the product/item, provided instructional content used to resolve the detected user frustration, timestamp data, and any received user feedback. Accordingly, the wearable-based instructional content delivery program 160 may compare the previously tracked and received wearable data from the knowledgebase/corpus to the tracked and received real-time data that includes the body sensor data such as the user continuously placing their arms/hands towards their cars, the elevated biometric data, and user speech such as, "ugh, these headphones won't connect to my computer as well."

The wearable-based instructional content delivery program 160 may further compare other data such as product/item information to determine similarities between products/items. For example, the wearable-based instructional content delivery program 160 may determine that the type of product/item, i.e. headphone, matches a type of product/item in the knowledgebase/corpus of frustration indicators. The wearable-based instructional content delivery program 160 may further determine that, for that type of headphone and based on previously captured frustration events, users have typically experienced frustration at a certain step/point including connecting the headphones to a second device.

In turn, and using the machine learning model, the wearable-based instructional content delivery program 160 may determine that the continuous placing of the arms/hands towards cars in addition to the elevated biometric data reaching the certain threshold level are behavioral triggers indicating user frustration based on similar data in the knowledgebase/corpus of frustration indicators. The wearable-based instructional content delivery program 160 may also use the NLP and machine learning algorithms associated with the machine learning model to contextualize and interpret the speech including, "ugh, these headphones won't connect to my computer as well." Similarly, in turn, the wearable-based instructional content delivery program 160 may determine that the context associated with the speech may be similarly compared to a context from similar speech in the knowledgebase/corpus indicating a behavioral trigger indicative of user frustration and a frustration event.

Accordingly, at 214, in response to determining that the tracked and received real-time wearable data associated with the user and the user activity indicates a user frustration event based on the comparison to the previously tracked and received wearable data associated with the user and other users from the knowledgebase/corpus of frustration indicators, the wearable-based instructional content delivery program 160 may retrieve and present instructional content from instructional material related to the user activity and the user frustration event. As previously described, for example, the wearable-based instructional content delivery program 160 may identify the specific type of headphone and, in turn, may identify and retrieve instructional material associated with the specific type of headphone. The wearable-based instructional content delivery program 160 may also determine the specific step and/or activity that is causing the user frustration based on the tracked real-time user data and the comparison to the previously tracked user data. For example, using the NLP and machine learning algorithms on the speech—"ugh, these headphones won't connect to my computer as well"—the wearable-based instructional content delivery program 160 may similarly interpret such speech and determine that the user is attempting to connect the purchased headphones to a device and/or simultaneously to a second device.

In turn, and as depicted at 216, the wearable-based instructional content delivery program 160 may identify, retrieve, and tailor specific instructional content from the instructional material related to the user activity and the specific step (including trying to connect headphones). For example, the instructional content may include specific step-by-step instructions related to the user activity for resolving an identified issue associated with the user activity. Thus, according to one embodiment, the instructional content may start at an optimal step for providing clear instructions to the user which may further be based on previously captured and correlated data from the knowledgebase/corpus of frustration indicators. According to one embodiment, the wearable-based instructional content delivery program 160 may also automatically present the instructional content on one or more computer devices associated with a user based on user preferences and/or may first prompt the user on the wearable device at 214. For example, the prompt may include a presented question on a display of the wearable device such as, "Would you like help with your current activity" or "Would you like help with your current item," as well as include selectable user interface icons that include "Yes" and "No." As previously described, in response to selecting "Yes," the wearable-based instructional content delivery program 160 may proceed with providing the identified and tailored instructional content. As previously described, in certain instances in which the machine learning model is uncertain on which instructional content to provide (which, again, may be based on a threshold percentage, such as the machine learning model having less than a 86% certainty), the wearable-based instructional content delivery program 160 may further prompt the user on the wearable device by asking the user to "provide additional information".

As previously described, based on user preferences, the wearable-based instructional content delivery program 160 may specifically provide the instructional content to the user by presenting the instructional content via audio on the wearable device and/or providing the instructional content on one or more other computer devices associated with the user such as displaying the instructional content on a mobile phone.

It may be appreciated that FIG. 2 provide only illustrations of one implementation and does not imply any limitations with regard to how different embodiments may be implemented. Many modifications to the depicted environments may be made based on design and implementation requirements.

As previously described, the present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Furthermore, machine learning as described herein may broadly refer to machine learning algorithms that learn from data. More specifically, machine learning is a branch of artificial intelligence that relates to algorithms such as mathematical models that can learn from, categorize, and make predictions about data. Such mathematical models, which can be referred to as machine-learning models, can classify input data among two or more classes; cluster input data among two or more groups; predict a result based on input data; identify patterns or trends in input data; identify a distribution of input data in a space; or any combination of these. Examples of machine-learning models can include (i) neural networks; (ii) decision trees, such as classification trees and regression trees; (iii) classifiers, such as Naïve bias classifiers, logistic regression classifiers, ridge regression classifiers, random forest classifiers, least absolute shrinkage and selector (LASSO) classifiers, and support vector machines; (iv) clusters, such as k-means clusters, mean-shift clusters, and spectral clusters; (v) factorization machines, principal component analyzers and kernel principal component analyzers; and (vi) ensembles or other combinations of machine-learning models. Neural networks can include deep neural networks, feed-forward neural networks, recurrent neural networks, convolutional neural networks, radial basis function (RBF) neural networks, echo state neural networks, long short-term memory neural networks, bi-directional recurrent neural networks, gated neural networks, hierarchical recurrent neural networks, stochastic neural networks, modular neural networks, spiking neural networks, dynamic neural networks, cascading neural networks, neuro-fuzzy neural networks, or any combination of these.

What is claimed is:

1. A computer-implemented method for automatically providing instructional content based on wearable data from a wearable device, comprising:

connecting and correlating the wearable device with one or more other computer devices associated with a user;

automatically tracking and receiving, via the wearable device and the one or more other computer devices, user data including internet data, messaging data, and user speech data, and identifying one or more items and corresponding item information specifically associated with the user from a user purchase based on the user data;

in response to identifying an item from the identified one or more items associated with the user, identifying and retrieving instructional material specifically associated with the item and storing the retrieved instructional material on at least one of a database and a cloud-based server;

automatically tracking and receiving, via the wearable device and based on the user data, real-time wearable data associated with the user and a detected user activity corresponding to an interaction with the item from the identified one or more items associated with the user, wherein automatically tracking and receiving the real-time wearable data associated with the user and the detected user activity further comprises automatically detecting body sensor data associated with the user and aggregating the user data from the automatically tracked and received user data to determine the item associated with the user and whether the user is interacting with the item;

based on the detected user activity corresponding to the interaction with the item, automatically determining, based on a machine learning model, whether the tracked and received real-time wearable data and the user data associated with the user and the detected user activity corresponding to the interaction with the item indicates a user frustration event based on a correlation between the user data including the user speech data, the real-time wearable data including the body sensor data, and a detection of a type of the item corresponding to the interaction with the item; and in response to automatically determining that the tracked and received real-time wearable data associated with the user and the user activity indicates the user frustration event, automatically retrieving and presenting the instructional content from the instructional material specifically related to the item.

2. The computer-implemented method of claim 1, wherein automatically tracking and receiving, via the wearable device and based on the user data, the real-time wearable data further comprises:

automatically tracking and receiving, via the wearable device, user movement data, user bodily position data, user location data, and the user speech data.

3. The computer-implemented method of claim 1, wherein automatically determining, based on the machine learning model, whether the tracked and received real-time wearable data and the user data associated with the user and the detected user activity corresponding to the interaction with the item indicates the user frustration event, further comprises:

comparing the tracked and received real-time wearable data to previously tracked and received wearable data and stored user frustration event data that is associated with the user and other users from a corpus of frustration event data.

4. The computer-implemented method of claim 3, further comprising:

training the machine learning model to identify and classify the previously tracked and received wearable data, wherein identifying and classifying the previously tracked and received wearable data further comprises identifying behavioral triggers from previously captured body sensor data that are indicative of the user frustration event.

5. The computer-implemented method of claim 4, further comprises:

storing the identified behavioral triggers from the previously captured body sensor data in the corpus of the frustration event data.

6. The computer-implemented method of claim 1, wherein presenting the instructional content from the instructional material related to the user activity and the user frustration event further comprises:

automatically presenting a prompt on the wearable device.

7. A computer system for automatically providing instructional content based on wearable data from a wearable device, comprising:

one or more processors, one or more computer-readable memories, one or more computer-readable tangible storage devices, and program instructions stored on at least one of the one or more storage devices for execution by at least one of the one or more processors via at least one of the one or more memories, wherein the computer system is capable of performing a method comprising:

connecting and correlating the wearable device with one or more other computer devices associated with a user;

automatically tracking and receiving, via the wearable device and the one or more other computer devices, user data including internet data, messaging data, and user speech data, and identifying one or more items and corresponding item information specifically associated with the user from a user purchase based on the user data;

in response to identifying an item from the identified one or more items associated with the user, identifying and retrieving instructional material specifically associated with the item and storing the retrieved instructional material on at least one of a database and a cloud-based server;

automatically tracking and receiving, via the wearable device and based on the user data, real-time wearable data associated with the user and a detected user activity corresponding to an interaction with the item from the identified one or more items associated with the user, wherein automatically tracking and receiving the real-time wearable data associated with the user and the detected user activity further comprises automatically detecting body sensor data associated with the user and aggregating the user data from the automatically tracked and received user data to determine the item associated with the user and whether the user is interacting with the item;

based on the detected user activity corresponding to the interaction with the item, automatically determining, based on a machine learning model, whether the tracked and received real-time wearable data and the user data associated with the user and the detected user activity corresponding to the interaction with the item indicates a user frustration event based on a correlation between the user data including the user speech data, the real-time wearable data including the body sensor data, and a detection of a type of the item corresponding to the interaction with the item; and in response to automatically determining that the tracked and received real-time wearable data associated with the user and the user activity indicates the user frustration event, automatically retrieving and presenting the instructional content from the instructional material specifically related to the item.

8. The computer system of claim 7, wherein automatically tracking and receiving, via the wearable device and based on the user data, the real-time wearable data further comprises:

automatically tracking and receiving, via the wearable device, user movement data, user bodily position data, user location data, and the user speech data.

9. The computer system of claim 7, wherein automatically determining, based on the machine learning model, whether the tracked and received real-time wearable data and the user data associated with the user and the detected user activity corresponding to the interaction with the item indicates the user frustration event, further comprises:

comparing the tracked and received real-time wearable data to previously tracked and received wearable data and stored user frustration event data that is associated with the user and other users from a corpus of frustration event data.

10. The computer system of claim 9, further comprising:

training the machine learning model to identify and classify the previously tracked and received wearable data, wherein identifying and classifying the previously tracked and received wearable data further comprises identifying behavioral triggers from previously captured body sensor data that are indicative of the user frustration event.

11. The computer system of claim 10, further comprises:

storing the identified behavioral triggers from the previously captured body sensor data in the corpus of the frustration event data.

12. The computer system of claim 7, wherein presenting the instructional content from the instructional material related to the user activity and the user frustration event further comprises:

automatically presenting a prompt on the wearable device.

13. A computer program product for automatically providing instructional content based on wearable data from a wearable device, comprising:

one or more tangible computer-readable storage devices and program instructions stored on at least one of the one or more tangible computer-readable storage devices, the program instructions executable by a processor, the program instructions comprising:

connecting and correlating the wearable device with one or more other computer devices associated with a user;

automatically tracking and receiving, via the wearable device and the one or more other computer devices, user data including internet data, messaging data, and user speech data, and identifying one or more items and corresponding item information specifically associated with the user from a user purchase based on the user data;

in response to identifying an item from the identified one or more items associated with the user, identifying and retrieving instructional material specifically associated with the item and storing the retrieved instructional material on at least one of a database and a cloud-based server;

automatically tracking and receiving, via the wearable device and based on the user data, real-time wearable data associated with the user and a detected user activity corresponding to an interaction with the item from the identified one or more items associated with the user, wherein automatically tracking and receiving the real-time wearable data associated with the user and the detected user activity further comprises automatically detecting body sensor data associated with the user and aggregating the user data from the automatically tracked and received user data to determine the item associated with the user and whether the user is interacting with the item;

based on the detected user activity corresponding to the interaction with the item, automatically determining, based on a machine learning model, whether the tracked and received real-time wearable data and the user data associated with the user and the detected user activity corresponding to the interaction with the item indicates a user frustration event based on a correlation between the user data including the user speech data, the real-time wearable data including the body sensor data, and a detection of a type of the item corresponding to the interaction with the item; and in response to automatically determining that the tracked and received real-time wearable data associated with the user and the user activity indicates the user frustration event, automatically retrieving and presenting the instructional content from the instructional material specifically related to the item.

14. The computer program product of claim 13, wherein automatically tracking and receiving, via the wearable device and based on the user data, the real-time wearable data further comprises:

automatically tracking and receiving, via the wearable device, user movement data, user bodily position data, user location data, and the user speech data.

15. The computer program product of claim 13, wherein automatically determining, based on the machine learning model, whether the tracked and received real-time wearable data and the user data associated with the user and the detected user activity corresponding to the interaction with the item indicates the user frustration event, further comprises:

comparing the tracked and received real-time wearable data to previously tracked and received wearable data and stored user frustration event data that is associated with the user and other users from a corpus of frustration event data.

16. The computer program product of claim 15, further comprising:

training the machine learning model to identify and classify the previously tracked and received wearable data, wherein identifying and classifying the previously tracked and received wearable data further comprises identifying behavioral triggers from previously captured body sensor data that are indicative of the user frustration event.

17. The computer program product of claim 16, further comprises:

storing the identified behavioral triggers from the previously captured body sensor data in the corpus of the frustration event data.

* * * * *